US012251503B2

(12) United States Patent
Lee et al.

(10) Patent No.: US 12,251,503 B2
(45) Date of Patent: Mar. 18, 2025

(54) SCREEN EXCHANGE DEVICE, BIOLOGICAL TISSUE SIZE REDUCTION SYSTEM COMPRISING SAME, BIOLOGICAL TISSUE SIZE REDUCTION METHOD USING SAME, AND METHOD FOR SEPARATING TARGET SUBSTANCE FROM RELEVANT BIOLOGICAL TISSUE

(71) Applicant: Jun Seok Lee, Busan (KR)

(72) Inventors: Jun Seok Lee, Busan (KR); Hasim Eray Copcu, Izmir (TR)

(73) Assignee: Jun Seok Lee, Busan (KR)

( * ) Notice: Subject to any disclaimer, the term of this patent is extended or adjusted under 35 U.S.C. 154(b) by 897 days.

(21) Appl. No.: 17/281,999

(22) PCT Filed: Apr. 8, 2020

(86) PCT No.: PCT/KR2020/004773
§ 371 (c)(1),
(2) Date: Apr. 1, 2021

(87) PCT Pub. No.: WO2020/209609
PCT Pub. Date: Oct. 15, 2020

(65) Prior Publication Data
US 2021/0353837 A1    Nov. 18, 2021

(30) Foreign Application Priority Data

Apr. 9, 2019 (KR) .......................... 10-2019-0041337
Oct. 22, 2019 (KR) .......................... 10-2019-0131097

(51) Int. Cl.
*A61M 1/02*    (2006.01)
*A61M 1/00*    (2006.01)

(52) U.S. Cl.
CPC .......... *A61M 1/029* (2013.01); *A61M 1/0272* (2013.01); *A61M 1/0281* (2013.01); *A61M 1/67* (2021.05)

(58) Field of Classification Search
None
See application file for complete search history.

(56) References Cited

U.S. PATENT DOCUMENTS 5,480,553 A    1/1996    Yamamori et al.
6,139,757 A    10/2000   Ohmura et al.
(Continued)

FOREIGN PATENT DOCUMENTS

CN    101516272    8/2009
CN    107107068    8/2017
(Continued)

OTHER PUBLICATIONS

"International Search Report (Form PCT/ISA/210) of PCT/KR2020/004773," mailed on Oct. 29, 2020, with English translation thereof, pp. 1-6.

*Primary Examiner* — Susan S Su
*Assistant Examiner* — Katherine-Ph Minh Pham
(74) *Attorney, Agent, or Firm* — JCIPRNET

(57) ABSTRACT

A screen exchange device for reducing the size of a biological tissue according to one embodiment comprises: a disk comprising a plurality of screens each having at least one through-hole configured to reduce the size of a biological tissue, the screens having different through-hole characteristics; a first cover which covers a first side of the disk and includes a first opening through which a biological tissue passes; a second cover which covers a second side of the disk and includes a second opening through which the biological tissue passes; a housing configured to receive the disk; and a manipulator which selects any one screen among the plurality of screens and manipulates the first cover or the (Continued)

second cover such that the selected screen communicates with the first opening and the second opening.

18 Claims, 11 Drawing Sheets

(56) References Cited

U.S. PATENT DOCUMENTS

| | | | |
|---|---|---|---|
| 8,780,191 | B2 | 7/2014 | Otsuka |
| 10,173,220 | B2 | 1/2019 | Middlebrook et al. |
| 2002/0197631 | A1 | 12/2002 | Lawrence et al. |
| 2004/0158226 | A1 | 8/2004 | Soo Hoo et al. |
| 2006/0142773 | A1 | 6/2006 | Sengun et al. |
| 2014/0008311 | A1* | 1/2014 | Weston ................. B01D 33/01 210/120 |
| 2016/0333305 | A1* | 11/2016 | Pilkington ............. C12M 45/02 |

FOREIGN PATENT DOCUMENTS

| | | | |
|---|---|---|---|
| CN | 108432391 | | 8/2018 |
| CN | 108949522 | | 12/2018 |
| JP | H10137557 | | 5/1998 |
| JP | 2006082816 | | 3/2006 |
| JP | 2007111653 | | 5/2007 |
| JP | 2009183149 | | 8/2009 |
| JP | 2009183149 A * | | 8/2009 ............ C12M 47/04 |
| KR | 100748487 | | 8/2007 |
| KR | 20190026586 | | 3/2019 |
| WO | 0013590 | | 3/2000 |
| WO | WO-2016097960 A2 * | | 6/2016 ............ B02C 18/10 |
| WO | 2019050251 | | 3/2019 |

\* cited by examiner

SCREEN EXCHANGE DEVICE, BIOLOGICAL TISSUE SIZE REDUCTION SYSTEM COMPRISING SAME, BIOLOGICAL TISSUE SIZE REDUCTION METHOD USING SAME, AND METHOD FOR SEPARATING TARGET SUBSTANCE FROM RELEVANT BIOLOGICAL TISSUE

CROSS-REFERENCE TO RELATED APPLICATION

This application is a 371 of international application of PCT application serial no. PCT/KR2020/004773, filed on Apr. 8, 2020, which claims the priority benefits of Korea application no. 10-2019-0041337, filed on Apr. 9, 2019, and Korea application no. 10-2019-0131097, filed on Oct. 22, 2019. The entirety of each of the above-mentioned patent applications is hereby incorporated by reference herein and made a part of this specification.

TECHNICAL FIELD

The following description relates to embodiments relate to a screen exchange device, a biological tissue size reducing system including a same, a biological tissue size reducing method using a same, and a method of separating a target material from a biological tissue associated therewith.

BACKGROUND ART

A biological tissue contains various tissues, cells, and materials that can be used for regenerative treatment and cosmetic purposes, and various methods are used to separate them. In particular, for adipose tissue, a method of decomposing and centrifuging the tissue using enzymes is widely used. However, there is a controversy over the safety of materials obtained from the adipose tissue degraded using the enzymes as still there is no appropriate medical enzyme and the enzyme used is toxic. Accordingly, various attempts have been made to obtain materials that can be used for regenerative treatment and cosmetic purposes from the adipose tissue without using enzymes. For example, U.S. Pat. No. 5,480,553 discloses a hollow fiber membrane module.

DISCLOSURE OF INVENTION

Technical Subject

An aspect of the present disclosure provides a screen exchange device that minimizes coupling and decoupling to a container containing a biological tissue, a biological tissue size reduction system including a same, and a biological tissue size reduction method using a same.

Another aspect of the present disclosure provides a method for effectively separating various target materials having various sizes and proportions from a biological tissue.

Technical Solution

According to an aspect of the present disclosure, there is provided a screen exchange device including a disk including a plurality of screens, each having at least one through-hole to reduce a size of a biological tissue, the screens having different through-hole characteristics, a first cover that covers a first side of the disk and includes a first opening through which a biological tissue passes, a second cover that covers a second side of the disk and includes a second opening through which the biological tissue passes, a housing configured to receive the disk, and a manipulator configured to select a screen from the plurality of screens and manipulate the first cover or the second cover such that the selected screen communicates with the first opening and the second opening.

The manipulator may include a first handle configured to rotate the first cover relative to the disk and a second handle configured to rotate the second cover relative to the disk.

The first handle may be operably coupled to the first cover so that the first cover is located at either a locking position at which a rotation of the first cover relative to the disk is locked or an operating position at which a rotation of the first cover relative to the disk is allowed. The second handle may be operably coupled to the second cover so that the second cover is located at either a locking position at which a rotation of the second cover relative to the disk is locked or an operating position at which a rotation of the second cover relative to the disk is allowed.

Each of the first handle and the second handle may include a central portion, a radial extension portion that extends from the central portion, and a circumferential extension portion that extends in a direction intersecting with an extension direction of the radial extension portion.

The circumferential extension portion may include an engagement element configured to engage with an inner surface of the housing.

The through-hole characteristics may include at least one selected from a group including a shape of the through-hole, a size of the through-hole, a depth of the through-hole, a position of a through-hole formed in a screen, an angle of a partial section of the through-hole with respect to the screen, and when the through-hole is provided as a plurality of through-holes, an arrangement of the plurality of through-holes.

Each of the plurality of screens may include a protrusion that protrudes from an edge defining the through-hole toward the first cover or the second cover while forming an angle with respect to a screen and is configured to scratch and tear a biological tissue passing through the through-hole.

The screen exchange device may further include a first spacer disposed between the first cover and the disk and a second spacer disposed between the second cover and the disk.

The first cover may further include a third opening through which a biological tissue passes. The second cover may further include a fourth opening through which a biological tissue passes.

The at least one through-hole may have an edge, and the edge may contact a biological tissue passing through the through-hole, press the biological tissue, and scratch and tear the biological tissue to reduce a size of the biological tissue.

According to another aspect of the present disclosure, there is also provided a system for reducing a size of a biological tissue, the system including the screen exchange device, a first syringe including a first container configured to be coupled to the first opening and receive a biological tissue and a first push rod configured to apply pressure to the first container, and a second syringe comprising a second container configured to be coupled to the second opening and receive a biological tissue and a second push rod configured to apply pressure to the second container, wherein the system takes a form between a first form in which, in response to the first push rod applying the pressure to the first container, the biological tissue of the first container moves to the second container by passing through the first opening, the selected screen, and the second opening in sequence and a second form in which, in response to the second push rod applying the pressure to the second container, the biological tissue of the second container moves to the first container by passing through the second opening, the selected screen, and the first opening in sequence.

According to another aspect of the present disclosure, there is also provided a method of reducing a size of a biological tissue, the method including coupling a first syringe and a second syringe each comprising at least a biological tissue to the first opening and the second opening of the screen exchange device, selecting a first screen from the plurality of screens using the manipulator, primarily reducing a size of a biological tissue while moving the biological tissue to the second syringe through the first opening, the first screen, and the second opening by pressing the first syringe and while moving a biological tissue to the first syringe through the second opening, the first screen, and the first opening by pressing the second syringe, selecting a second screen from the plurality of screens using the manipulator, and secondarily reducing the size of the biological tissue while moving the biological tissue to the second syringe through the first opening, the second screen, and the second opening by pressing the first syringe and while moving a biological tissue to the first syringe through the second opening, the second screen, and the first opening by pressing the second syringe.

The method may further include reducing a size of a biological tissue by sequentially selecting a plurality of remaining screens having through-hole characteristics different from a through-hole characteristic of the first screen and a through-hole characteristic of the second screen from the plurality of screens after the secondarily reducing of the size of the biological tissue.

According to another aspect of the present disclosure, there is also provided a method for separating a target material from a biological tissue, the method including a first centrifugation step of centrifuging a biological tissue at a first centrifugal acceleration to remove a non-target material and obtain a plurality of types of materials comprising a target material, a step of reducing a size of a remaining biological tissue by sequentially selecting a plurality of screens having different through-hole characteristics, a second centrifugation step of centrifuging the plurality of types of materials including the remaining biological tissue at a second centrifugal acceleration different from the first centrifugal acceleration, and a first separation step of separating a material layer containing a target material.

The step of reducing the size of the remaining biological tissue may be repetitively performed a plurality of times.

The method may further include a step of removing air in a size-reduced biological tissue after the step of reducing the size of the biological tissue.

The method may further include a step of compressing a size-reduced biological tissue and separating a material containing a target material from a biological tissue after the step of reducing the size of the biological tissue.

The method may further include a step of mixing a set solution in the separated material layer and reducing sizes of materials contained in a mixed solution using a screen having a set through-hole characteristic.

The method may further include a third centrifugation step of centrifuging the mixed solution at a third centrifugal acceleration different from the first centrifugal acceleration and the second centrifugal acceleration and a second separation step of separating a material layer containing a target material.

The method may further include a step of removing air in a mixture of the separated material layer and a set solution.

The method may further include a third centrifugation step of centrifuging the mixed solution at a third centrifugal acceleration greater than the first centrifugal acceleration and greater than or equal to the second centrifugal acceleration and a second separation step of separating a material layer containing a target material.

Effects

According to an embodiment, a screen exchange device, a biological tissue size reduction system including a same, and a biological tissue size reduction method using a same may minimize coupling and decoupling to a container containing a biological tissue.

According to an embodiment, a method may effectively separate various target materials having various sizes and proportions from a biological tissue.

Effects of a screen exchange device, a biological tissue size reduction system including a same, a biological tissue size reduction method using a same, and a method of separating a target material from a biological tissue associated therewith are not limited to the above-mentioned effects, and other effects that are not mentioned will be clearly understood by those skilled in the art from the description of the scope of the claims.

BEST MODE FOR CARRYING OUT THE INVENTION

Figure 1:
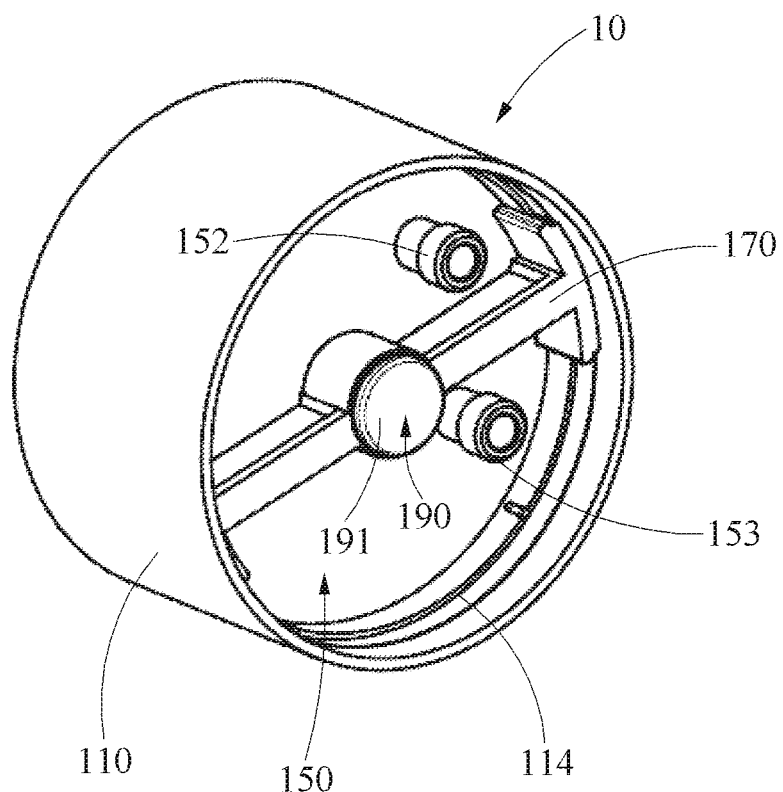
FIG. 1 is a perspective view illustrating a screen exchange device viewed from one direction according to an embodiment.
Figure 2:
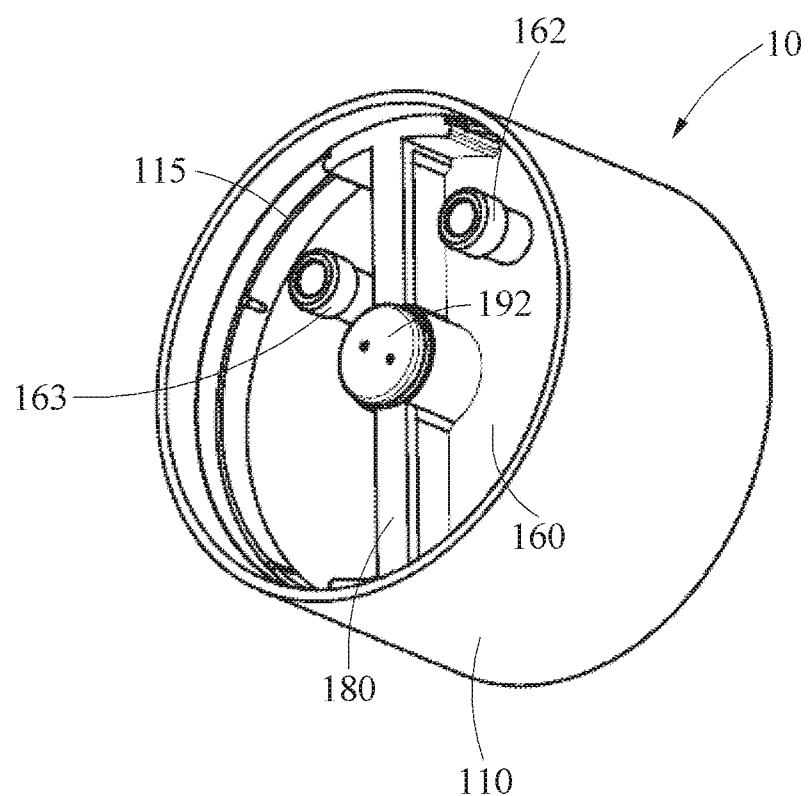
FIG. 2 is a perspective view illustrating a screen exchange device viewed from the other direction according to an embodiment.
Figure 3:
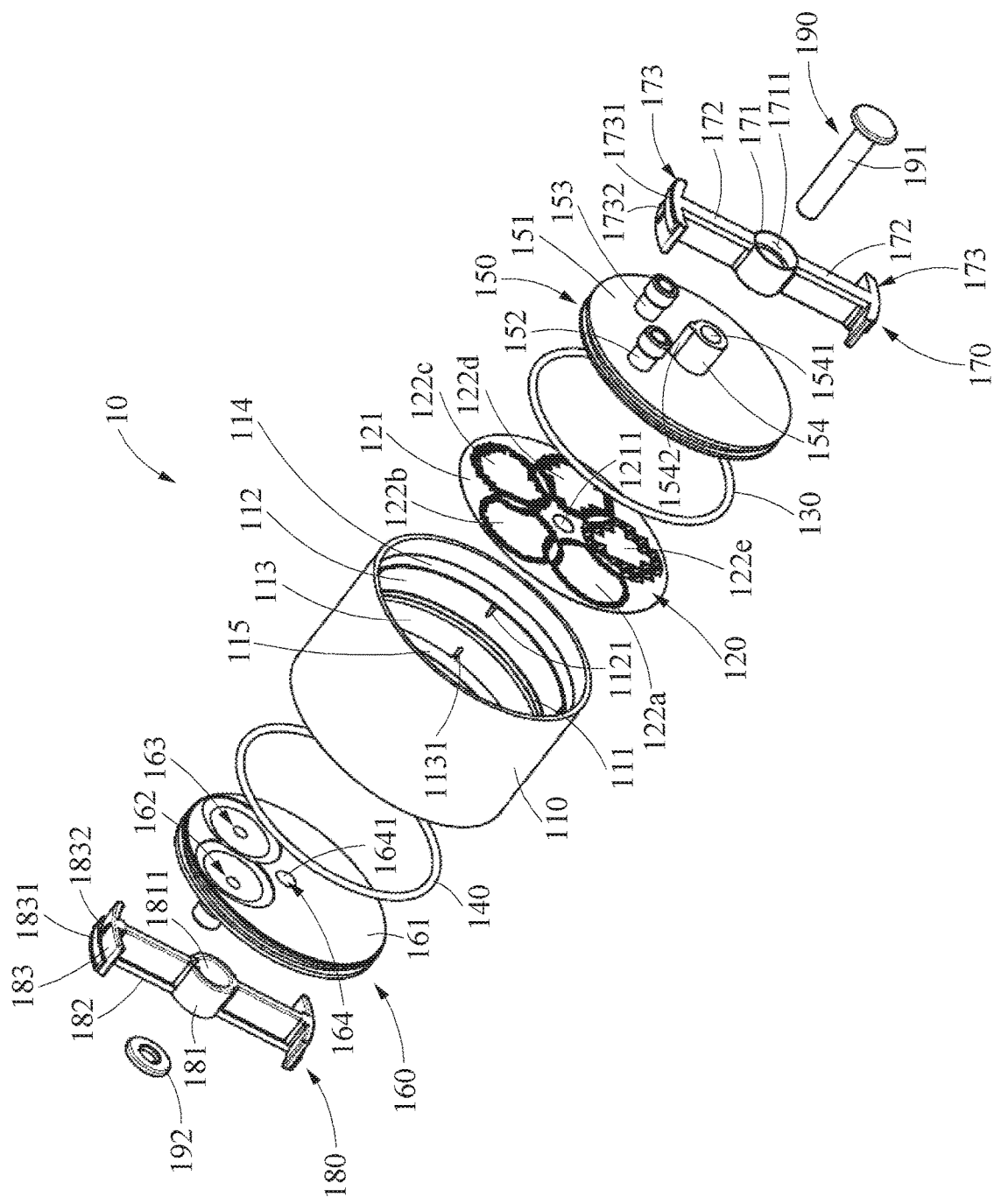
FIG. 3 is an exploded perspective view illustrating a screen exchange device according to an embodiment.
Figure 4:
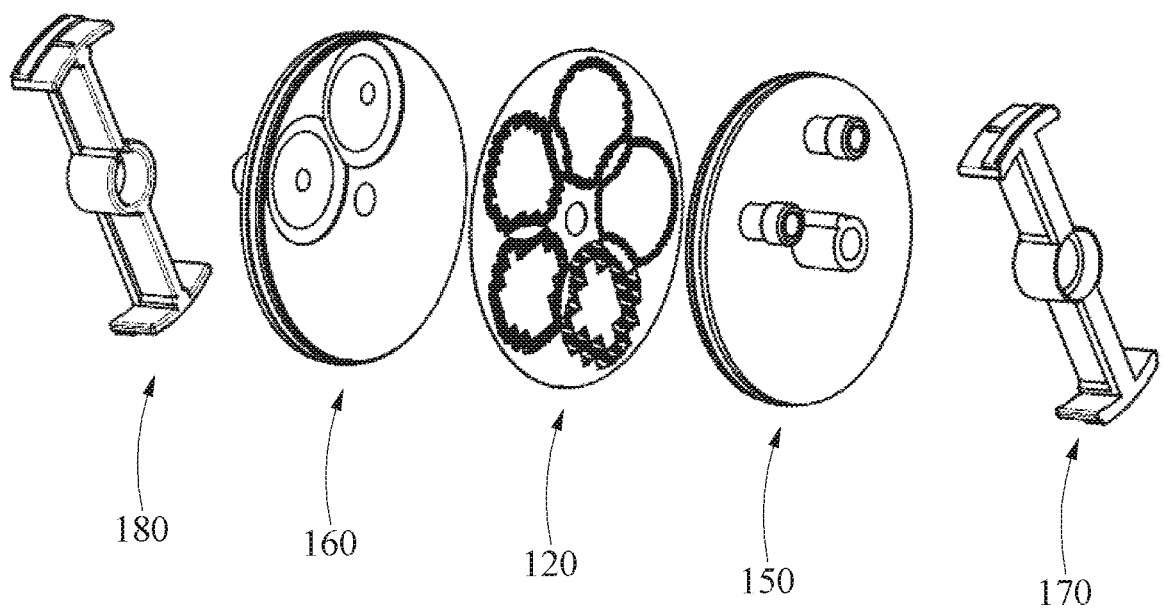
FIG. 4 is an exploded perspective view illustrating some components of a screen exchange device according to an embodiment.
Figure 5:
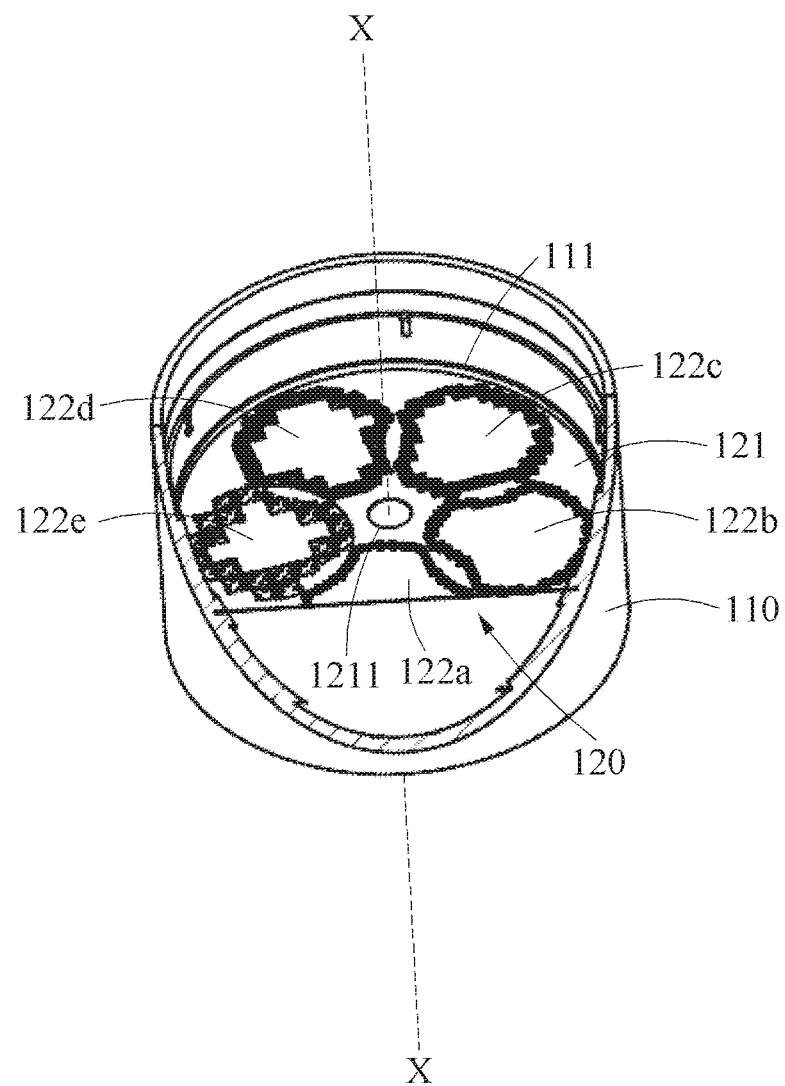
FIG. 5 is a cutaway perspective view illustrating a partial structure of a screen exchange device according to an embodiment.

Hereinafter, embodiments will be described in detail with reference to the accompanying drawings. It should be understood, however, that there is no intent to limit this disclosure to the particular embodiments disclosed. On the contrary, embodiments are to cover all modifications, equivalents, and alternatives falling within the scope of the embodiments.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

A component having a common function with a component included in one embodiment is described using a like name in another embodiment. Unless otherwise described, a description made in one embodiment may be applicable to another embodiment and a detailed description within a duplicate range is omitted.

Referring to FIGS. 1 through 5, a screen exchange device 10 according to an embodiment may select a first screen 122a from a plurality of screens 122a, 122b, 122c, 122d, and 122e, each including a plurality of through-holes configured to reduce a size of a biological tissue, reduce the size of the biological tissue using the selected first screen 122a, select a second screen 122b from the plurality of screens 122a, 122b, 122c, 122d, and 122e, and reduce the size of the biological tissue using the selected second screen 122b. Here, the selection and the order of the plurality of screens 122a, 122b, 122c, 122d, and 122e is determined by a user and thus, a screen selection and order are not limited to the foregoing. Also, the biological tissue may be, for example, an adipose tissue but is not limited thereto.

The screen exchange device 10 may include a housing 110, a disk 120, a first sealing portion 130, a second sealing portion 140, a first cover 150, a second cover 160, manipulators 170 and 180, and a support 190.

The housing 110 may receive the disk 120, the first sealing portion 130, the second sealing portion 140, the first cover 150, and the second cover 160. The housing 110 may seal the disk 120 from outside along with the first sealing portion 130 and the second sealing portion 140. The housing 110 may have a substantially cylindrical shape. The housing 110 may have a first side open and a second side that is open and opposite the first side.

The housing 110 may include a first mount 111, a second mount 112, a third mount 113, a first slot 114, and a second slot 115.

The disk 120 may be mounted on the first mount 111. In an exemplary embodiment, the disk 120 may be fixed to the first mount 111. In this embodiment, the disk 120 may rotate along with the housing 110. The first mount 111 may be formed in an inner surface of a middle portion of the housing 110.

The first sealing portion 130 and the first cover 150 may be mounted on the second mount 112. The second mount 112 may be formed in an inner surface on the first side based on the middle portion of the housing 110.

The second sealing portion 140 and the second cover 160 may be mounted on the third mount 113. The third mount 113 may be formed in an inner surface on the second side based on the middle portion of the housing 110, the second side being opposite the first side.

A first circumferential extension portion 173 of a first handle 170 may be mounted on the first slot 114. In an exemplary embodiment, the first circumferential extension portion 173 of the first handle 170 may unlockably engage with the first slot 114. Also, the first slot 114 may allow the first circumferential extension portion 173 to move in a circumferential direction. The first slot 114 may be formed in the inner surface on the first side of the housing 110 to be adjacent to the second mount 112.

A second circumferential extension portion 183 of a second handle 180 may be mounted on the second slot 115. In an exemplary embodiment, the second circumferential extension portion 183 of the second handle 180 may unlockably engage with the second slot 115. Also, the second slot 115 may allow a movement of the second circumferential extension portion 183. The second slot 115 may be formed in the inner surface of the second side of the housing 110 to be adjacent to the third mount 113.

In an X-axis direction corresponding to a longitudinal direction of the housing 110, the first slot 114, the second mount 112, the first mount 111, the third mount 113, and the second slot 115 may be sequentially formed in the inner surface of the housing 110.

The disk 120 may include a plate 121 and the plurality of screens 122a, 122b, 122c, 122d, and 122e. The plate 121 may be fixed to the first mount 111. The plate 121 may include a first central opening 1211. The plate 121 may have a substantially circular cross-section. The plurality of screens 122a, 122b, 122c, 122d, and 122e may be spaced apart from one another in a circumferential direction of the plate 121 based on the first central opening 1211 and installed in the plate 121.

The plate 121, for example, a partial section corresponding to the plurality of screens 122a, 122b, 122c, 122d, and 122e, may be spaced apart from the first cover 150 and the second cover 160 by a clearance distance. The clearance distance between the plate 121 and the first cover 150 and the clearance distance between the plate 121 and the second cover 160 may define a free space between the plate 121 and the first cover 150 and a free space between the plate 121 and the second cover 160, respectively. In the free spaces, a portion of the biological tissue may flow.

Each of the plurality of screens 122a, 122b, 122c, 122d, and 122e may include at least one through-hole to reduce a size of the biological tissue. The plurality of screens 122a, 122b, 122c, 122d, and 122e may have different through-hole characteristics. Here, the through-hole characteristics may include a shape of the through-hole, a size of the through-hole, a depth of the through-hole, a position of a through-hole formed in a screen, an angle of a partial section of the through-hole with respect to the plate 121, and when the through-hole is provided as a plurality of through-holes, an arrangement of the plurality of through-holes. Accordingly, the plurality of screens 122a, 122b, 122c, 122d, and 122e having different through-hole characteristics may indicate that through-holes of the plurality of screens 122a, 122b, 122c, 122d, and 122e have different sizes, for example. Here, the size of the through-hole may refer to a maximum length of the through-hole across the through-hole. For example, when the through-hole has a circular shape, the size of the through-hole may be a diameter of the through-hole. Meanwhile, the shape of the through-hole may be a circular shape, a polygonal shape, or a shape composed of a plurality of edges.

The first sealing portion 130 may perform sealing between the disk 120 and the first cover 150. The first sealing portion 130 may be disposed between the disk 120 and the first cover 150 and installed in the inner surface of the housing 110 along a circumference of the housing 110. The first sealing portion 130 may have a ring shape.

The second sealing portion 140 may perform sealing between the disk 120 and the second cover 160. The second sealing portion 140 may be disposed between the disk 120 and the second cover 160 and installed in the inner surface of the housing 110 along the circumference of the housing 110. The second sealing portion 140 may have a ring shape.

The first cover 150 may cover the first side of the disk 120.

According to an embodiment, the first cover 150 may include a first base 151, a first connector 152 having a first opening, and a first fastener 154. The first base 151 may have a substantially circular cross-section. The first opening of the first connector 152 may allow the biological tissue to pass therethrough. The first opening may penetrate the first base 151. The first connector 152 may be connected to a container containing the biological tissue or an empty container. The first connector 152 may protrude from the first base 151. The first connector 152 may be formed on a periphery of the first base 151. The first handle 170 may be fastened to the first fastener 154. The first fastener 154 may include a first fastening hole 1541 through which a first locker 191 of the support 190 passes and a first guide 1542 that guides an X-axial movement of the first handle 170. The first fastener 154 may be formed in a central portion of the first base 151.

In one embodiment, the first cover 150 may further include a third connector 153 having a third opening. The third opening of the third connector 153 may allow the biological tissue to pass therethrough. The third connector 153 may be connected to a container containing the biological tissue or an empty container. The third connector 153 may protrude from the first base 151. In addition, the third connector 153 may be formed in the first base 151 to be spaced apart from the first connector 152. Also, the third connector 153 may be formed on the periphery of the first base 151. The third opening of the third connector 153 may communicate with a screen having a through-hole with a largest width among the plurality of screens 122a, 122b, 122c, 122d, and 122e. In this embodiment, a user may connect the third connector 153 to a container containing a biological tissue in a form of a lump, pass the biological tissue through the third opening, roughly reduce a size of the biological tissue using the screen having the through-hole with the largest width, connect the container to the first connector 152, select a screen having a desired through-hole characteristic from the plurality of screens 122a, 122b, 122c, 122d, and 122e, and reduce the size of the biological tissue using the selected screen.

The second cover 160 may cover the second side opposite the first side of the disk 120. In one embodiment, the second cover 160 may include a second base 161, a second connector 162 having a second opening, and a second fastener 164. The second fastener 164 may include a second fastening hole and a second guide (not shown). In one embodiment, the second cover 160 may further include a fourth connector 163 having a fourth opening. Unless otherwise stated in the present disclosure, it can be understood that structures, functions, and effects of the second base 161, the second connector 162, the fourth connector 163, and the second fastener 164 of the second cover 160 are substantially the same as the above-described structures, functions, and effects of the first base 151, the first connector 152, the third connector 153, and the first fastener 154 of the first cover 150.

The manipulators 170 and 180 may select at least one screen from the plurality of screens 122a, 122b, 122c, 122d, and 122e and manipulate the first cover 150 and the second cover 160 such that the selected screen communicates with the first opening of the first connector 152 and the second opening of the second connector 162, or the third opening of the third connector 153 and the fourth opening of the fourth connector 163.

The manipulators 170 and 180 may include the first handle 170 and the second handle 180. Although the description is given of the manipulators 170 and 180 including the first handle 170 and the second handle 180, the manipulators 170 and 180 may include only one of the first handle 170 and the second handle 180. Also, in some cases, the functions of the manipulators 170 and 180 may be performed in other possible mechanical methods, electronic methods, and the like not described herein.

The first handle 170 may manipulate the first cover 150 such that the first cover 150 rotates relative to the disk 120. The first handle 170 may include a first central portion 171, a first radial extension portion 172, and the first circumferential extension portion 173. The first central portion 171 may be fastened to the first fastener 154. The first central portion 171 may move along the first guide 1542 of the first fastener 154. The first central portion 171 may include a second central opening 1711 through which the first locker 191 of the support 190 passes. The second central opening 1711 may be aligned with the first fastening hole 1541 of the first fastener 154. The first radial extension portion 172 may extend from the first central portion 171 in a radial direction of the first cover 150. The first circumferential extension portion 173 may extend in a direction intersecting with a direction in which the first radial extension portion 172 extends. The first circumferential extension portion 173 may have an arc shape based on the first central portion 171 as a center.

The first circumferential extension portion 173 may move along the inner surface of the housing 110 and unlockably engage with the inner surface of the housing 110. The first circumferential extension portion 173 may include a first movement element 1731 and a first engagement element 1732. The first movement element 1731 may circumferentially move along the first slot 114 of the housing 110. The first engagement element 1732 may engage with a first recess 1121 of the second mount 112 of the housing 110.

When the first central portion 171 moves along the first guide 1542 and the first cover 150 is located at a locked position, the first engagement element 1732 may engage with the first recess 1121 of the second mount 112 of the housing 110. At this time, when the user manipulates the first handle 170 to rotate the first cover 150 with the first handle 170 coupled, because the first engagement element 1732 is engaged with the first recess 1121 of the second mount 112, a rotation of the first cover 150 relative to the housing 110 and the disk 120 fixed to the housing 110 may be locked.

Meanwhile, when the first central portion 171 moves along the first guide 1542 and the first cover 150 is located at an operating position, the first engagement element 1732 may be unlocked from the first recess 1121 of the second mount 112 of the housing 110. At this time, when the user manipulates the first handle 170 to rotate the first cover 150 coupled with the first handle 170 with respect to the axis X, because the first engagement element 1732 is unlocked from the first recess 1121 of the second mount 112, rotation of the first cover 150 relative to the housing 110 and the disk 120 fixed to the housing 110 may be allowed. The user may align the first opening of the first connector 152 and the third connector 153 with a desired screen among the plurality of screens 122*a*, 122*b*, 122*c*, 122*d*, and 122*e* while rotating the first cover 150 with respect to the axis X by manipulating the first handle 170.

The second handle 180 may manipulate the second cover 160 such that the second cover 160 rotates relative to the disk 120. The second handle 180 may include a second central portion 181, a second radial extension portion 182, and the second circumferential extension portion 183. The second circumferential extension portion 183 may include a second movement element 1831 that moves along the inner surface of the second slot 115 of the housing 110 and a second engagement element 1832 that engages with a second recess 1131 of the third mount 113 of the housing 110. Unless otherwise stated in the present disclosure, it can be understood that structures, functions, and effects of the second central portion 181, the second radial extension portion 182, and the second circumferential extension portion 183 of the second handle 180 are substantially the same as the above-described structures, functions, and effects of the first central portion 171, the first radial extension portion 172, and the first circumferential extension portion 173 of the first handle 170.

In one embodiment, the first handle 170 and the second handle 180 may be interlocked with each other. Here, the first handle 170 and the second handle 180 interlocked with each other may indicate that the first handle 170 and the second handle 180 may be directly or indirectly connected to each other so that, in accordance with one of the first handle 170 and the second handle 180 being manipulated, a remaining one operates along therewith. For example, the first handle 170 and the second handle 180 may be connected through the first locker 191 of the support 190. In this example, when the user rotates the first handle 170 with respect to the axis X, the second handle 180 may rotate along with the first handle 170 while the housing 110 and the disk 120 are stationary.

In one embodiment, the first handle 170 and the second handle 180 may operate independently. Here, the first handle 170 and the second handle 180 independent of each other may indicate a characteristic that the first handle 170 and the second handle 180 are not connected to each other so that an operation of the first handle 170 and manipulation of the second handle 180 are not dependent on each other. For example, the first handle 170 and the second handle 180 may be configured not to interfere with each other by the first locker 191 of the support 190. In this example, when rotating the first handle 170 with respect to the axis X at a first angle, the user may rotate the second handle 180 with respect to the axis X at a second angle different from the first angle. Here, the direction in which the first handle 170 and the second handle 180 rotates with respect to the axis X may be the same direction or different directions.

The support 190 may support the first handle 170, the first cover 150, the second cover 160, and the second handle 180. The support 190 may include the first locker 191 and a second locker 192. The first locker 191 may pass through the second central opening 1711, the first fastening hole 1541, the first central opening 1211, a second fastening hole 1641, and a third central opening 1811 and coupled to the second locker 192. Through this, the first handle 170, the first cover 150, the second cover 160, and the second handle 180 may rotate based on the axis X relative to the housing 110 and the disk 120 without eccentricity (stationary).

Figure 6:
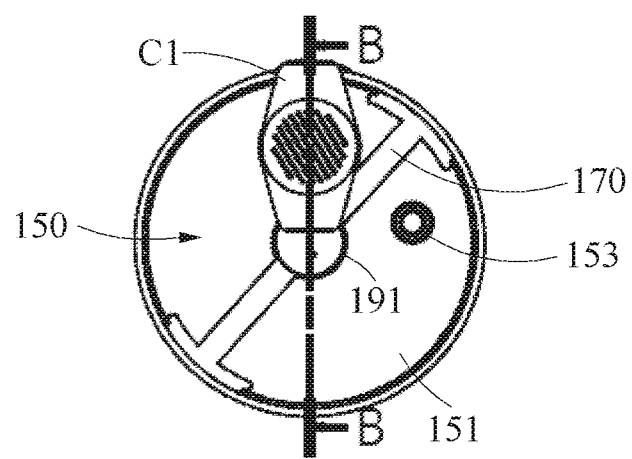
FIG. 6 is a top view illustrating a screen exchange device included in a system for reducing a size of a biological tissue according to an embodiment.
Figure 7:
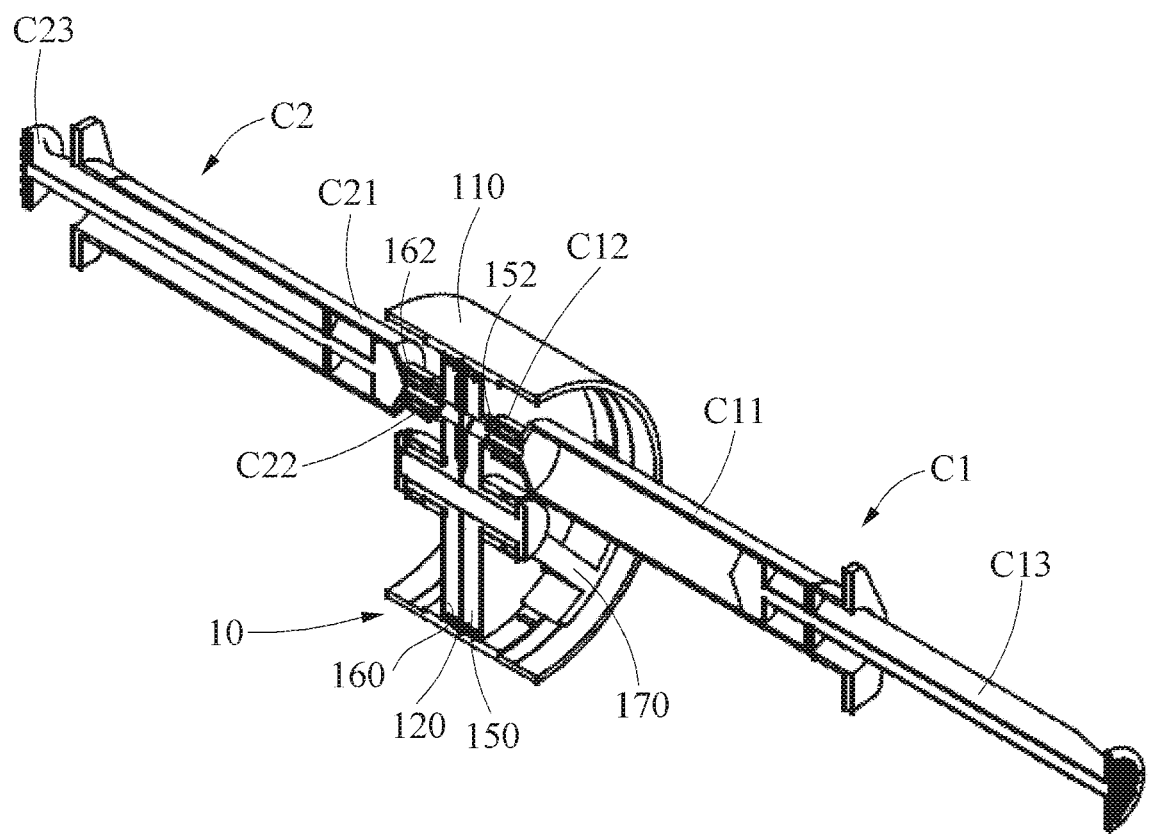
FIG. 7 is a cross-sectional perspective view of the screen exchange device of FIG. 6 taken along line B-B.
Figure 8:
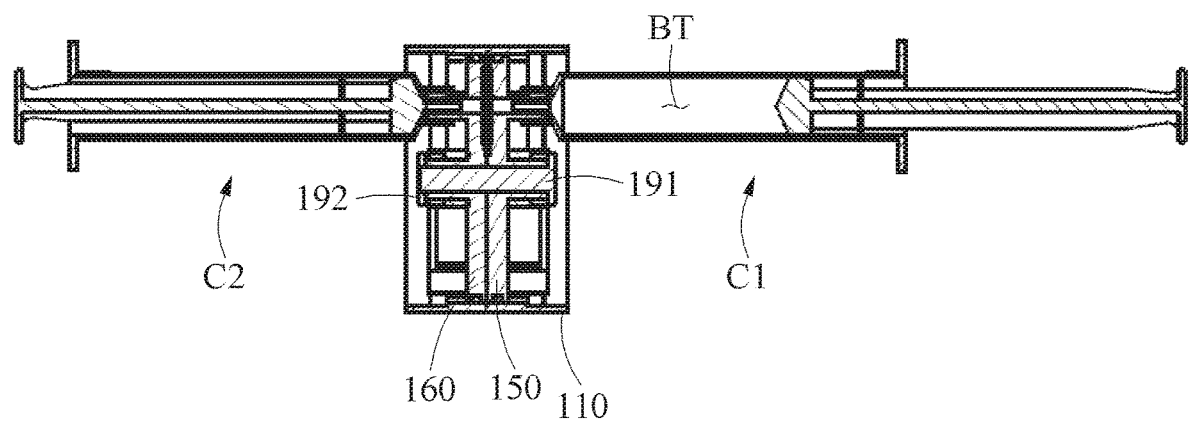
FIG. 8 is a cross-sectional front view of the screen exchange device of FIG. 6 taken along line B-B.

Referring to FIGS. 6 through 8, a system 1 for reducing a size of a biological tissue according to an embodiment may include the screen exchange device 10, a first syringe C1, and a second syringe C2.

The first syringe C1 may include a first container C11 that receives a biological tissue BT, a first coupling portion C12 formed in a front end portion of the first container C11 to be coupled to the first connector 152 or the third connector 153 of the first cover 150, and a first push rod C13 that applies pressure to an inside of the first container C11 and presses the biological tissue BT toward the disk 120.

The second syringe C2 may include a second container C21 that receives the biological tissue BT, a second coupling portion C22 formed in a front end portion of the second container C21 to be coupled to the second connector 162 or the fourth connector 163 (refer to FIGS. 2 and 3) of the second cover 160, and a second push rod C23 that applies pressure to an inside of the second container C21 and presses the biological tissue BT toward the disk 120.

In one example of operation, a user puts the biological tissue BT to be reduced in size into the first container C11 and couples the first coupling portion C12 to the first connector 152. After that, the user couples the second coupling portion C22 of the second container C21 empty to the second connector 162. After that, the user manipulates the first handle 170 in an axial direction such that the first cover 150 is located at an operating position. After that, the user rotates the first cover 150 by rotating the first handle 170 with respect to the axial direction and selects a desired screen from a plurality of screens such that the screen having a desired through-hole characteristic communicates with the first opening of the first connector 152 and the second opening of the second connector 162.

After that, the user manipulates the second handle 180 in the axial direction such that the second cover 160 is located at the operating position. After that, the user rotates the second cover 160 by rotating the second handle 180 in the axial direction and selects the same screen as the previously selected screen such that the screen having the desired through-hole characteristic communicates with the second opening of the second connector 162 and the first opening of the first connector 152.

After that, the user presses the biological tissue BT toward the disk 120 using the first push rod C13. In this process, the biological tissue BT may be reduced in size while passing through the selected screen of the disk 120 so that the second push rod C23 is retracted as the biological tissue BT moves to the second container C21. Likewise, the user may press the biological tissue BT toward the disk 120 using the second push rod C23. In this process, the biological tissue BT may be reduced in size while passing through the selected screen so that the first push rod C13 is retracted as the biological tissue BT moves to the first container C11. The user may repetitively press the first push rod C13 and the second push rod C23 as described above. Through this, the biological tissue BT may repetitively pass through the screen and be reduced in size.

Selectively, in the above-described process of reducing the size of the biological tissue BT, the user may rotate the first handle 170 and the second handle 180 degrees, select another screen having another through-hole characteristic, and repeat the foregoing process, thereby reducing the size of the biological tissue BT.

Selectively, before putting the biological tissue BT into the first container C11 and coupling the first coupling portion C12 to the first connector 152 as described above, the user may couple the first coupling portion C12 to the third connector 153. At this time, the third opening of the third connector 153 may be aligned with a screen having at least one through-hole with a greatest width. After that, the user couples the second coupling portion C22 of the second container C21 to the fourth connector 163 (refer to FIGS. 2 and 3). Here, the fourth connector 163 may be aligned with the previously selected screen. After that, the user roughly reduces the size of the biological tissue BT using the first push rod C13 and the second push rod C23 in the same manner as described above. After that, the user separates the first container C11 and the second container C21, couples the first coupling portion C12 and the second coupling portion C22 to the first connector 152 and the second connector 162, respectively, and repeats the process of reducing the size as described above.

Figure 9:
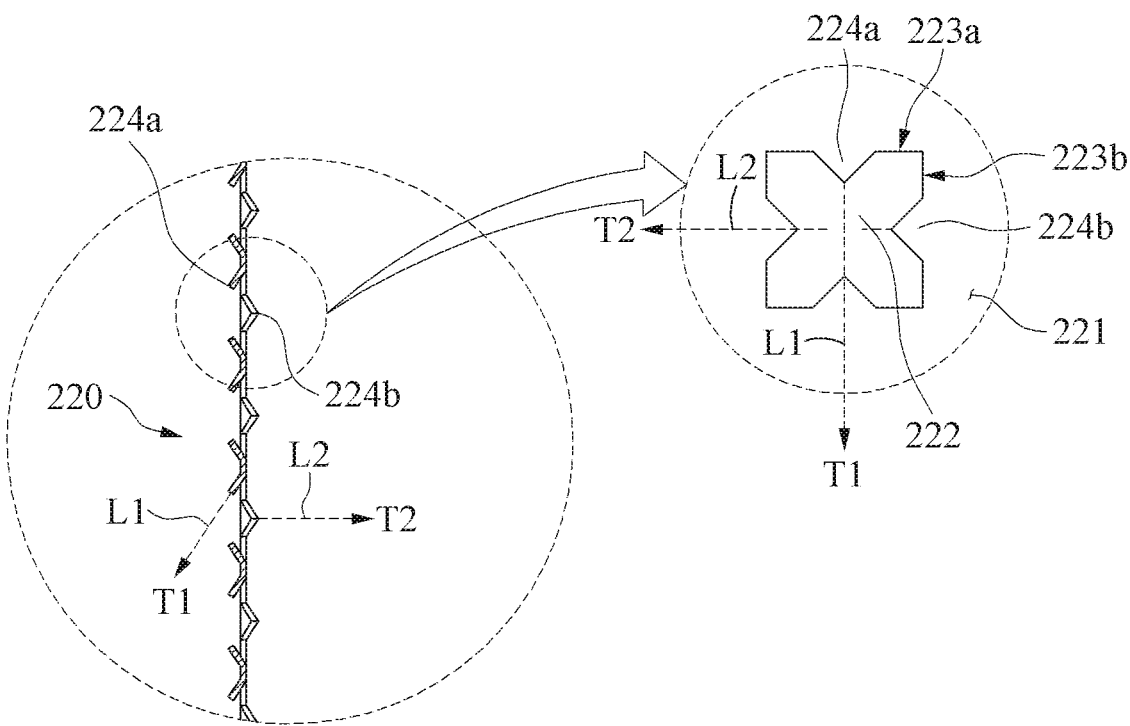
FIG. 9 is a diagram illustrating a screen according to an embodiment.

FIG. 9 is a diagram illustrating a screen according to an embodiment.

Referring to FIG. 9, a screen 220 according to an embodiment may include a plate 221 and a through-hole 222. The through-hole 222 may be defined by a plurality of edges of the plate 221. The edges may contact a biological tissue passing through the through-hole 222, press the biological tissue, and scratch and tear the biological tissue, thereby reducing a size of the biological tissue. For example, the screen 220 may include a first linear portion 223a formed at a first side of the through-hole 222, a first protrusion 224a formed at the first side of the through-hole 222 and protruding toward a center of the through-hole 222 in a first direction T1, a second linear portion 223b formed at a second side of the through-hole 222, and a second protrusion 224b formed at the second side of the through-hole 222 and protruding toward the center of the through-hole 222 in a second direction T2, so as to increase a section of an edge contacting tissues passing through a through-hole. The first protrusion 224a and the second protrusion 224b may be oriented at an angle to the screen 220 and configured to scratch and tear the biological tissue passing through the screen 220. A first extension line L1 of the first protrusion 224a protruding in the first direction T1 and a second extension line L2 of the second protrusion 224b protruding in the second direction T2 may be in a twisted position. In other words, the first extension line L1 and the second extension line L2 may not be parallel to each other and may not meet each other. The direction T1 of the first protrusion 224a and the direction T2 of the second protrusion 224b may be set such that the first protrusion 224a and the second protrusion 224b face one of the first cover 150 and the second cover 160.

Figure 10:
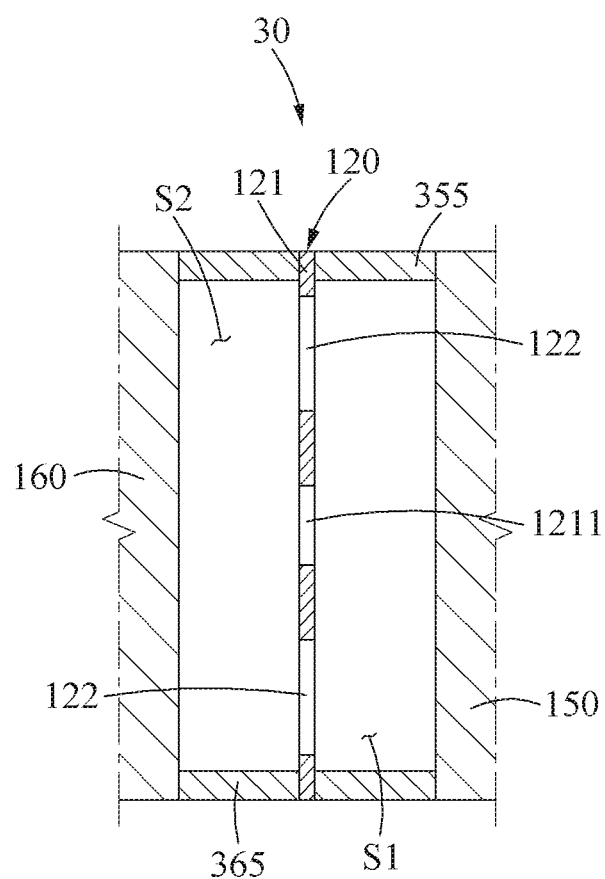
FIG. 10 is a diagram illustrating an example of a partial structure of a screen exchange device according to an embodiment.

FIG. 10 is a cross-sectional view illustrating an example of a partial structure of a screen exchange device according to an embodiment.

Referring to FIG. 10, a screen exchange device 30 according to an embodiment may include a first spacer 355 disposed between the disk 120 and the first cover 150 and a second spacer 365 disposed between the disk 120 and the second cover 160. The first spacer 355 may be configured to secure a first space S1 between the disk 120 and the first cover 150. The second spacer 365 may be configured to secure a second space S2 between the disk 120 and the second cover 160.

The first spacer 355 and the second spacer 365 may be formed of any material suitable for securing the first space S1 and the second space S2. As an example, the first spacer 355 and the second spacer 365 may include a metal material. In this example, sizes of the first space S1 and the second space S2 may be maintained to be substantially the same during an operation of the screen exchange device 30. As another example, the first spacer 355 and the second spacer 365 may include an elastic material. In this example, the sizes of the first space S1 and the second space S2 may vary during the operation of the screen exchange device 30.

The first spacer 355 and the second spacer 365 may have any appropriate shape that does not interfere with rotation of the covers 150 and 160 and size reduction of the biological tissue. For example, the first spacer 355 and the second spacer 365 may have an annular shape.

The first spacer 355 and the second spacer 365 may be arranged outward the plurality of screens 122 circumferentially arranged around the first central opening 1211 of the plate 121.

Figure 11:
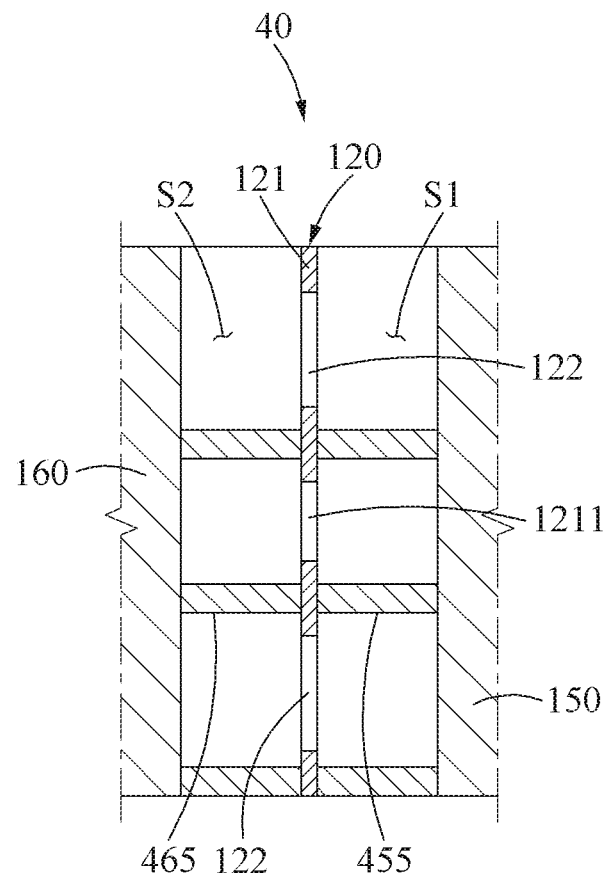
FIG. 11 is a diagram illustrating another example of a partial structure of a screen exchange device according to an embodiment.

FIG. 11 is a cross-sectional view illustrating another example of a partial structure of a screen exchange device according to an embodiment.

Referring to FIG. 11, a screen exchange device 40 according to an embodiment may include a first spacer 455 disposed between the disk 120 and the first cover 150 and a second spacer 465 disposed between the disk 120 and the second cover 160. A difference from the embodiment of FIG. 10 is that, in the embodiment of FIG. 11, the first spacer 455 and the second spacer 465 are arranged inward the plurality of screens 122 circumferentially arranged around the first central opening 1211 of the plate 121.

Hereinafter, a method of reducing a size of a biological tissue, separating a tissue, a cell, and a target material, and removing a non-target material will be described. Here, the non-target material is understood as an unnecessary material. The following examples relate to separating a stromal vascular fraction (SVF) from an adipose tissue. However, a method of separating a biological tissue is not limited to the examples.

Example 1

[Process 1] First, centrifugation is performed on obtained fat at a low speed (RCF 50 g to 300 g).

[Process 2] After the centrifugation, material layers such as blood urea and fluid are removed.

[Process 3] Thereafter, an adipose tissue is reduced in size by scratching and tearing the adipose tissue using the screen exchange device described above, and a combination of tissues, cells, and materials constituting the adipose tissue is separated.

[Process 4] Thereafter, to separate the adipose tissue and the tissues, cells, and materials of the adipose tissue again, centrifugation is performed on the tissues, cells, and materials at a high speed (RCF 500 g to 2000 g).

[Process 5] After the centrifugation, a material layer containing an SVF gathered at a position farther from a center of rotation compared to an adipose material layer is separated.

[Process 6] A process of removing air mixed with adipose tissues and materials after performing process 3 may be added.

[Process 7] In process 3, a screen having a through-hole of 300 μm to 4000 μm is selected from a plurality of screens of the screen exchange device to scratch and tear the adipose tissue.

[Process 8] In process 7, a first step of selecting a screen having a through-hole of 3000 μm to 4000 μm and reducing a size of an adipose tissue, a second step of selecting a screen having a through-hole of 2000 μm to 3000 μm and reducing a size of an adipose tissue, a third step of selecting a screen having a through-hole of 1000 μm to 2000 μm and reducing a size of an adipose tissue, and a fourth step of selecting a screen having a through-hole of 500 μm to 1000 μm and reducing a size of an adipose tissue may be performed in sequence.

[Process 9] In process 8, after the fourth step, a fifth step of selecting a screen having a through-hole of 300 μm to 500 μm and reducing the size of the adipose tissue may be added.

[Process 10] A biological tissue may be reduced in size by moving the adipose tissue back and forth to pass through the through-hole of the screen 5 to 50 times for each step of process 8 and process 9.

[Process 11] After performing process 5, the separated materials may be filtered through a screen and a filter having a through-hole of 50 μm to 200 μm.

[Process 12] After performing process 5, saline or distilled water is mixed with the separated material layer, and then a screen having a through-hole of 500 μm to 1000 μm may be selected to refine the mixed material layer.

[Process 13] In process 12, the biological tissue may be reduced in size by moving the mixed material layer back and forth 5 to 50 times to pass through the through-hole of the screen using the selected screen of the screen exchange device.

[Process 14] After process 12, centrifugation may be performed at a high speed (RCF 500 g to 3000 g) to separate the mixed material layer and the material separated therefrom.

[Process 15] After process 14, a material layer containing an SVF gathered at a position farthest from the center of rotation may be separated.

Example 2

[Process 1] First, centrifugation is performed on an obtained adipose tissue at a low speed (RCF 50 g to 300 g).

[Process 2] After the centrifugation, material layers such as blood urea and fluid are removed.

[Process 3] Thereafter, the adipose tissue is reduced in size by scratching and tearing the adipose tissue using the screen exchange device described above, and a combination of tissues, cells, and materials constituting the adipose tissue is separated.

[Process 4] Thereafter, the size-reduced adipose tissue is compressed to obtain the tissues, cells, and materials separated from the adipose tissue.

[Process 5] Thereafter, to separate the tissues, cells, and materials separated from the adipose tissue once again, centrifugation is performed on the materials at a high speed (RCF 500 g to 2000 g).

[Process 6] After the centrifugation, a material layer containing an SVF gathered at a position farthest from the center of rotation is separated.

[Process 7] A process of removing air mixed with adipose tissues and materials after performing process 3 may be added.

[Process 8] In process 3, a screen having a through-hole of 300 μm to 4000 μm is selected from a plurality of screens of the screen exchange device to scratch and tear the adipose tissue.

[Process 9] In process 8, a first step of selecting a screen having a through-hole of 3000 μm to 4000 μm and reducing a size of an adipose tissue, a second step of selecting a screen having a through-hole of 2000 μm to 3000 μm and reducing a size of an adipose tissue, a third step of selecting a screen having a through-hole of 1000 μm to 2000 μm and reducing a size of an adipose tissue, and a fourth step of selecting a screen having a through-hole of 500 μm to 1000 μm and reducing a size of an adipose tissue may be performed in sequence.

[Process 10] In process 9 after the fourth step, a fifth step of selecting a screen having a through-hole of 300 μm to 500 μm and reducing the size of the adipose tissue may be added.

[Process 11] A biological tissue may be reduced in size by moving the adipose tissue back and forth to pass through the through-hole of the screen 5 to 50 times for each step of process 9 and process 10.

[Process 12] After performing process 6, the separated materials may be filtered using a filter and a screen having a through-hole of 50 μm to 200 μm.

[Process 13] After performing process 6, saline or distilled water is mixed with the separated material layer, and then a screen having a through-hole of 500 μm to 1000 μm may be selected to refine the mixed material layer.

[Process 14] In process 13, tissues, cells, and materials included in a mixed material may be reduced in size by moving the mixed material layer back and forth 5 to 50 times to pass through the through-hole of the screen.

[Process 15] After process 13, centrifugation may be performed at a high speed (RCF 500 g to 3000 g) to separate the mixed material layer and the material separated therefrom.

[Process 16] After process 15, a material layer containing an SVF gathered at a position farthest from the center of rotation may be separated.

The above-described method may sufficiently obtain a target material originating from a biological tissue by scratching and tearing the biological tissue such that a size of the biological tissue is gradually reduced while minimizing a damage to a stem cell originating from a biological tissue. Here, the biological tissue may include an adipose tissue.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

The invention claimed is:

1. A screen exchange device comprising:
   a disk comprising a plurality of screens, each having at least one through-hole to reduce a size of a biological tissue, the screens having different through-hole characteristics;
   a first cover that covers a first side of the disk and comprises a first opening through which a biological tissue passes;
   a second cover that covers a second side of the disk and comprises a second opening through which the biological tissue passes;
   a housing configured to receive the disk, the first cover and the second cover; and
   a manipulator configured to select a screen from the plurality of screens and manipulate the first cover or the second cover such that the selected screen communicates with the first opening and the second opening, wherein the manipulator is disposed inside the housing, wherein the manipulator comprises:
      a first handle configured to rotate the first cover relative to the disk; and
      a second handle configured to rotate the second cover relative to the disk.

2. The screen exchange device of claim 1, wherein the first handle is operably coupled to the first cover so that the first cover is located at either a locking position at which a rotation of the first cover relative to the disk is locked or an operating position at which a rotation of the first cover relative to the disk is allowed, and
   the second handle is operably coupled to the second cover so that the second cover is located at either a locking position at which a rotation of the second cover relative to the disk is locked or an operating position at which a rotation of the second cover relative to the disk is allowed.

3. The screen exchange device of claim 1, wherein each of the first handle and the second handle comprises:
   a central portion;
   a radial extension portion that extends from the central portion; and
   a circumferential extension portion that extends in a direction intersecting with an extension direction of the radial extension portion.

4. The screen exchange device of claim 3, wherein the circumferential extension portion comprises an engagement element configured to engage with an inner surface of the housing.

5. The screen exchange device of claim 1, wherein the through-hole characteristics comprises at least one selected from a group comprising a shape of the through-hole, a size of the through-hole, a depth of the through-hole, a position of a through-hole formed in a screen, an angle of a partial section of the through-hole with respect to the screen, and when the through-hole is provided as a plurality of through-holes, an arrangement of the plurality of through-holes.

6. The screen exchange device of claim 1, wherein each of the plurality of screens comprises a protrusion that protrudes from an edge defining the through-hole toward the first cover or the second cover while forming an angle with respect to a screen and is configured to scratch and tear a biological tissue passing through the through-hole.

7. The screen exchange device of claim 1, further comprising:
   a first spacer disposed between the first cover and the disk; and
   a second spacer disposed between the second cover and the disk.

8. The screen exchange device of claim 1, wherein the first cover further comprises a third opening through which a biological tissue passes, and
   the second cover further comprises a fourth opening through which a biological tissue passes.

9. The screen exchange device of claim 1, wherein the at least one through-hole has an edge, and
   the edge contacts a biological tissue passing through the through-hole, presses the biological tissue, and scratches and tears the biological tissue to reduce a size of the biological tissue.

10. A system for reducing a size of a biological tissue, the system comprising:
    a screen exchange device, comprising:
       a disk comprising a plurality of screens, each having at least one through-hole to reduce a size of a biological tissue, the screens having different through-hole characteristics;
       a first cover that covers a first side of the disk and comprises a first opening through which a biological tissue passes;
       a second cover that covers a second side of the disk and comprises a second opening through which the biological tissue passes;
       a housing configured to receive the disk, the first cover and the second cover; and
       a manipulator configured to select a screen from the plurality of screens and manipulate the first cover or the second cover such that the selected screen communicates with the first opening and the second opening, wherein the manipulator is disposed inside the housing, wherein the manipulator comprises:
          a first handle configured to rotate the first cover relative to the disk; and
          a second handle configured to rotate the second cover relative to the disk:
    a first syringe comprising a first container configured to be coupled to the first opening and receive a biological tissue and a first push rod configured to apply pressure to the first container; and
    a second syringe comprising a second container configured to be coupled to the second opening and receive a biological tissue and a second push rod configured to apply pressure to the second container,
    wherein the system takes a form between a first form in which, in response to the first push rod applying the pressure to the first container, the biological tissue of the first container moves to the second container by passing through the first opening, the selected screen, and the second opening in sequence and a second form in which, in response to the second push rod applying the pressure to the second container, the biological tissue of the second container moves to the first container by passing through the second opening, the selected screen, and the first opening in sequence.

11. The system of claim 10, wherein the first handle is operably coupled to the first cover so that the first cover is located at either a locking position at which a rotation of the first cover relative to the disk is locked or an operating position at which a rotation of the first cover relative to the disk is allowed, and the second handle is operably coupled to the second cover so that the second cover is located at either a locking position at which a rotation of the second cover relative to the disk is locked or an operating position at which a rotation of the second cover relative to the disk is allowed.

12. The system of claim 10, wherein each of the first handle and the second handle comprises:
a central portion;
a radial extension portion that extends from the central portion; and
a circumferential extension portion that extends in a direction intersecting with an extension direction of the radial extension portion.

13. The system of claim 12, wherein the circumferential extension portion comprises an engagement element configured to engage with an inner surface of the housing.

14. The system of claim 10, wherein the through-hole characteristics comprises at least one selected from a group comprising a shape of the through-hole, a size of the through-hole, a depth of the through-hole, a position of a through-hole formed in a screen, an angle of a partial section of the through-hole with respect to the screen, and when the through-hole is provided as a plurality of through-holes, an arrangement of the plurality of through-holes.

15. The system of claim 10, wherein each of the plurality of screens comprises a protrusion that protrudes from an edge defining the through-hole toward the first cover or the second cover while forming an angle with respect to a screen and is configured to scratch and tear a biological tissue passing through the through-hole.

16. The system of claim 10, further comprising:
a first spacer disposed between the first cover and the disk; and
a second spacer disposed between the second cover and the disk.

17. The system of claim 10, wherein the first cover further comprises a third opening through which a biological tissue passes, and the second cover further comprises a fourth opening through which a biological tissue passes.

18. The system of claim 10, wherein the at least one through-hole has an edge, and the edge contacts a biological tissue passing through the through-hole, presses the biological tissue, and scratches and tears the biological tissue to reduce a size of the biological tissue.

* * * * *